United States Patent
Butterworth

(10) Patent No.: US 9,618,464 B2
(45) Date of Patent: Apr. 11, 2017

(54) METAL DETECTOR FOR PRODUCTION AND PACKAGING LINES

(71) Applicant: Mettler-Toledo Safeline Ltd., Manchester (GB)

(72) Inventor: Daren Butterworth, Manchester (GB)

(73) Assignee: Mettler-Toledo Safeline Ltd., Manchester (GB)

( * ) Notice: Subject to any disclaimer, the term of this patent is extended or adjusted under 35 U.S.C. 154(b) by 505 days.

(21) Appl. No.: 14/149,346

(22) Filed: Jan. 7, 2014

(65) Prior Publication Data

US 2014/0125311 A1    May 8, 2014

Related U.S. Application Data

(63) Continuation of application No. PCT/EP2012/063283, filed on Jul. 6, 2012.

(30) Foreign Application Priority Data

Jul. 8, 2011    (EP) .................................. 11173277

(51) Int. Cl.
- *G01N 27/00* (2006.01)
- *G01R 33/025* (2006.01)
- *G01V 3/10* (2006.01)

(52) U.S. Cl.
CPC .......... *G01N 27/00* (2013.01); *G01R 33/025* (2013.01); *G01V 3/10* (2013.01)

(58) Field of Classification Search
CPC .............................. G01N 27/00; G01V 3/105
See application file for complete search history.

(56) References Cited

U.S. PATENT DOCUMENTS

| | | | |
|---|---|---|---|
| 4,012,690 A * | 3/1977 | Heytow | ................. G01V 3/105 |
| 4,563,645 A | 1/1986 | Kerr | |
| 4,870,381 A * | 9/1989 | Moran | |
| 5,572,121 A | 11/1996 | Beswick | |
| 6,204,667 B1 | 3/2001 | Won | |
| 7,061,236 B2 | 6/2006 | Britton | |
| 7,893,690 B2 | 2/2011 | Simon | |

FOREIGN PATENT DOCUMENTS

| | | |
|---|---|---|
| CN | 2514010 Y | 10/2002 |
| CN | 201777434 U | 3/2011 |
| JP | 07092284 A * | 4/1995 |

* cited by examiner

*Primary Examiner* — Walter L Lindsay, Jr.
*Assistant Examiner* — Milton Gonzalez
(74) *Attorney, Agent, or Firm* — Standley Law Group LLP

(57) ABSTRACT

A metal detector (20) has a metallic enclosure (21) with entrance and exit apertures (30, 31). A coil system inside the enclosure has an energized transmitter coil. First and second receiver coils (24, 25) bound a detection zone (28) between the apertures, through which inspected objects (2) travel. The receiver coils are on opposite sides of the transmitter coil, with regard to the direction of travel (13). The receiver coils are connected in series, but their windings are wires oppositely in a rotational sense. Metal contamination in the object generates a detection signal in the receiver coils. A first and second flange (26), arranged at the entrance and exit, cancel the undesirable influence of metal contamination beyond a first distance upstream of and a second distance downstream of the coil system. The respective flanges differ from each other and, consequently, the first and second distances are different.

15 Claims, 2 Drawing Sheets

A. SIDE VIEW

B. TOP VIEW

METAL DETECTOR FOR PRODUCTION AND PACKAGING LINES

CROSS-REFERENCE TO RELATED APPLICATIONS

This application is a continuation of PCT/EP2012/063283, filed on 6 Jul. 2012, which in turn claims a right of priority under 35 USC §119 from European patent application 11173277.2, filed 8 Jul. 2011. The content of each application is incorporated by reference as if fully recited herein.

TECHNICAL FIELD

The invention relates to an industrial metal detector for the food-, beverage-, pharmaceuticals-, plastics-, chemicals-, packaging-, and other industries.

BACKGROUND

The main purpose of metal detectors of the kind described herein is to detect the presence of metal in an article, a bulk material, or generally any object being examined. Such metal detectors are widely used and integrated into production and packaging lines, for example to detect contamination of food by metal particles or components from broken processing machinery during the manufacturing process, which constitutes a major safety issue in the food industry. The generic type of metal detector that this invention relates to and which is known as balanced three-coil system with an encircling coil arrangement can be described as a portal through which the articles and materials under inspection are moving, for example individual packages riding on a horizontal conveyor belt through a vertical portal, or a stream of bulk material in free fall through a vertical duct or funnel passing through a horizontally arranged portal.

The portal is generally configured as a box-shaped metallic enclosure with an entrance aperture and an exit aperture. The operative part of the metal detector is a system of three electrical coils wound on a common hollow carrier or coil former made of a non-metallic material, which is arranged inside the metallic enclosure. The aperture cross-section of the coil former matches the size and shape of the entrance and exit apertures and lines up with them, so that the coil former and the entrance and exit apertures form a tunnel defining a detection zone through which the conveyor belt or other transport means moves the articles or materials under inspection. The cross-section of this detection zone tunnel is generally rectangular or circular, but could also have any other shape.

In state-of-the-art metal detectors of this type, the coils are exactly parallel to each other and, consequently, their parallel planes are orthogonal to their common central axis. The center coil, also variously called transmitter coil, emitter coil, or excitation coil, is connected to a high-frequency oscillator and thus generates a primary alternating electromagnetic field which, in turn, induces a first and a second alternating voltage, respectively, in the two coils on either side of the center coil, which are also called the first and the second receiver coil. The first and second receiver coils are connected in series with each other, but with their windings wired in opposition to each other. In other words, the coil wire runs continuously from a first output terminal through the windings of the first receiver coil, then with the opposite sense of rotary direction through the windings of the second receiver coil to a second output terminal. In addition the first and second receiver coils are located equidistant from the transmitter coil. Therefore, they are in all respects mirror images of each other in relation to the central plane of the transmitter coil, and thus the first and the second alternating voltage induced in them by the primary alternating electromagnetic field will cancel each other. In other words, the mirror symmetry of this state-of-the-art metal detector has the result that the voltage picked up between the first and second output terminals will be zero.

Symmetrical balance coil arrangements can also consist of multiple transmitter coils and/or multiple receiver coils that are arranged in such a way to achieve a so called null balance condition. Therefore the first receiver coil can form one or more entrance-side receiver coils, and the second receiver coil one or more exit-side receiver coils. Likewise the transmitter coil can be designed as one or more transmitter coils.

However, if a piece of metal passes through the coil arrangement, the electromagnetic field is disturbed, giving rise to a dynamic voltage signal across the output terminals of the serially connected receiver coils.

The foregoing concept, often referred to as "balanced-coil system", "inductively balanced metal detector" and similar terms, is commonly known in the field of industrial metal detectors. The generic principle is described and illustrated for example in U.S. Pat. No. 4,563,645 (col. 1, lines 11-32, and FIG. 1) as well as U.S. Pat. No. 7,061,236 B2 (col. 1, lines 20-41, and FIGS. 1 and 2a).

The metallic enclosure surrounding the coil arrangement serves to prevent airborne electrical signals or nearby metallic items and machinery from interfering with the proper functioning of the metal detector. In addition, the metal enclosure adds strength and rigidity to the assembly, which is absolutely essential as even microscopic dislocations of the coils relative to each other and relative to the enclosure can disturb the detection system which is sensitive to signals in the nanovolt range.

An issue of concern in metal detectors of the foregoing description is their sensitivity to stationary and, even more so, to moving metal in areas outside the detection zone and, in particular, even far outside the enclosure of the metal detector. This is due to the fact that the electromagnetic field generated by the transmitter coil extends outside the entrance and exit apertures to a distance as far as two or three times the length of the detection zone. If there are stationary or moving metal parts within this range, for example the support frame or other components of a conveyor, the interaction of the electromagnetic field with the metallic parts in its reach will produce an unwanted output signal of the receiver coils which interferes with the actual detection signals originating from metallic contaminants in the material under inspection traveling through the metal detector. Therefore, unless special design measures are taken, a large space before the entrance aperture and after the exit aperture of the metal detector has to be kept free of all metal. The area that must be kept free of metal in order to ensure the proper operation of a balanced-coil metal detector is generally called the "metal-free zone" or MFZ.

The metal-free zone, in particular its length in the direction of the transport path, is normally specified as a multiple of the aperture height (or diameter) h for stationary metal and for moving metal. According to EP 0 536 288 B1 (col. 2, lines 6-8, and FIG. 1), the MFZ extends to about 1.5×h for stationary metal and to about 2×h for moving metal. In any given application, the MFZ will dictate the metal detector system design, specifically the insertion space, i.e. the amount of space that must be allowed in a packaging or process line to accommodate the metal detector and its MFZ.

In applications where the space available for the metal detector is limited and where the foregoing guideline can therefore not be met, the interference due to metallic objects in the ambient vicinity could be suppressed by lowering the sensitivity of the metal detector to the point where the spurious signals are no longer registered. Of course, this would simultaneously reduce the useful detection sensitivity for metal contaminants inside the detection zone, i.e. it would handicap the metal detector in a clearly undesirable way.

A solution whereby the metal-free zone in the type of metal detector described hereinabove is reduced or even eliminated is presented in EP 0 536 288 B1, which is hereby incorporated by reference in the present disclosure. One of the possible means for reducing or eliminating the MFZ described in EP 0 536 288 B1 has the form of metallic flanges or collars that may be integral with the rims of the entrance and exit apertures of the enclosure of the metal detector. These flanges or collars act as short-circuit coils in which a current is induced by the alternating electromagnetic field of the transmitter coil. The induced current, in turn, generates a secondary electromagnetic field which can, under certain conditions, nullify the primary field of the transmitter coil beyond a certain distance before the entrance coil and after the exit coil, even to the extent that the primary field outside the apertures of the enclosure is totally suppressed and the metal-free zones before the entrance aperture and after the exit aperture are effectively reduced to zero providing a so-called "zero metal-free zone" (ZMFZ).

Because a state-of-the-art metal detector using the ZMFZ concept according to EP 0 536 288 B1 can be operated at the full detection sensitivity that it was designed for, even with metallic structures or machinery adjacent to one or both of its apertures, it is advantageous for installations where there is not enough space available to allow for the metal-free zones that would be required with a metal detector of an earlier state of the art. Nevertheless, the full sensitivity of a metal detector equipped with aperture flanges according to the ZMFZ concept is lower than the full sensitivity of a conventional metal detector operating with the required metal-free zones. Thus, the present state of the art still represents a compromise: while a ZMFZ metal detector significantly reduces or even eliminates the need for metal-free zones upstream and/or downstream in the processing line, it comes at the expense of a somewhat lower detection sensitivity in comparison to a conventional metal detector installed in a longer insertion space that allows for the metal-free zones.

SUMMARY

It is therefore the object of the present invention to provide an improved metal detector which employs the ZMFZ concept while approaching or matching the detection sensitivity of a conventional metal detector with standard metal-free zones.

This requirement is met by a metal detector having the features named in the independent patent claims. Various embodiments and refinements of the invention are presented in the dependent claims. Typical production- or packaging lines incorporating a metal detector according to the invention are presented in further claims.

The metal detector according to the present invention has a metallic enclosure with an entrance aperture and an exit aperture and, arranged inside the metallic enclosure, a coil system with at least one transmitter coil and at least one first and at least one second receiver coil. The entrance and exit apertures and the first and second receiver coils form a tunnel-like detection zone through which objects under inspection move along a travel path that enters the metal detector through the entrance aperture and leaves the metal detector through the exit aperture.

Preferably, relative to this travel path, the first receiver coil or coils are arranged ahead of the transmitter coil, and the second receiver coil or coils are arranged after the transmitter coil or coils. The first and second receiver coils are wired in series with each other, they have an equal small number of winding turns (typically a single turn), and they are wound with the opposite sense of rotation relative to each other.

The metal detector of the present invention comprises means for cancelling the primary field beyond a certain distance from the coil system. The means for cancelling the primary field are preferably configured in the form of metallic flanges or collars that are connected to, or integral with, the rims of the entrance and exit apertures of the metallic enclosure of the metal detector. The flanges or collars perform the function of short-circuit coils in which an alternating current is induced by the primary electromagnetic field of the transmitter coil. This induced current, in turn, generates a secondary electromagnetic field which nullifies the primary field of the transmitter coil beyond a certain distance from the coil system.

The metal detector of the present invention is distinguished from the prior art by the fact that the means for cancelling the primary field on the side of the entrance aperture and the means for cancelling the primary field on the side of the exit aperture are no longer equal and symmetric to each other relative to a central plane of the metal detector. In other words the metal detector of the present invention has a first cancelling means arranged at the entrance aperture and a different, second cancelling means arranged at the exit aperture. The first and second cancelling means differ from each other not only in their configuration, but also in their ability to cancel the primary electromagnetic field. Consequently, the primary field is cancelled beyond a first distance from the entrance aperture and beyond a different, second distance from the exit aperture. Accordingly, the metal detector according to the invention has a first metal-free zone which, relative to a travel path of said objects under inspection, extends upstream to a first distance from the entrance aperture, and a different second metal-free zone which extends downstream to a second distance from the exit aperture.

Due to the inductive interaction that takes place between the cancelling means and the coil system, the asymmetric cancelling means would result in a large imbalance between the voltages induced in the receiver coils of a symmetrical coil system. Therefore, the concept of asymmetric cancelling means first of all requires a solution to compensate for this voltage imbalance between the receiver coils without thereby disturbing the electrical signal circuit in other ways. In the process of the present invention, it was found that this problem can be solved if the first and second receiver coils are placed in asymmetric positions relative to the transmitter coil or coils and relative to the metallic housing and to the first and second cancelling means, wherein the asymmetric positions are determined so that the first and second voltages cancel each other when there is no metal present in said objects under inspection. In other words, the coil system is still a balanced coil system, but lacks the geometric symmetry of the coil systems in prior-art metal detectors.

Interestingly, a metal detector according to the invention showed improved sensitivity compared to a state-of-the-art metal detector using the ZMFZ concept according to EP 0 536 288 B1.

As balance coil arrangements can also consist of multiple transmitter coils and/or multiple receiver coils that are arranged in such a way to achieve a so called null balance condition, in the context of the following description and claims of the inventive concept, the term "transmitter coil" and/or "receiver coil" may stand for "at least one transmitter coil" and/or "at least one receiver coil".

In an exemplary embodiment the transmitter coil or coils are positioned in a central plane between the entrance aperture and the exit aperture and the receiver coils are arranged each at a different distance from the transmitter coil, i.e. asymmetrically with regard to their position from said central plane. Alternatively the transmitter coil is positioned out of center between the entrance aperture and the exit aperture whereas the receiver coils are arranged each at a different distance from the transmitter coil but not necessarily from said central plane.

Of particular interest is an embodiment of the foregoing concept where a cancelling means is present at only one of the apertures, so that the primary electromagnetic field is cancelled only on the side of one aperture of the metal detector while remaining essentially undiminished on the side of the other aperture. In a practical embodiment of what could be called a one-sided ZMFZ design, the transmitter coil is placed essentially halfway between the entrance and exit apertures, the receiver coil next to aperture that has no cancelling means is positioned so as to optimize the sensitivity of the coil system to metal contaminants in the objects under inspection, and the position of the receiver coil next to the aperture with the cancelling means is determined by computer modeling or experimentation, so that the coil system is electrically balanced.

The choice of a metal detector with an asymmetric configuration according to the foregoing description suggests itself specifically for installations where a packaging- or production apparatus unit containing metallic components is arranged in line with the metal detector and directly adjacent to either the entrance aperture or the exit aperture, and wherein few or no metallic components are present within a metal-free zone extending outside the other aperture. In such a situation, which is quite common, a metal detector according to the invention with either asymmetric or totally one-sided cancelling means can be used very advantageously in that the suppression of the primary field—and thus the reduction or elimination of the metal-free zone—can be concentrated on the side of the metal detector where it is needed, while the opposite side of the metal detector can be designed with the aim of optimizing the overall sensitivity of the metal detector.

In a metal detector according to the invention, the detection zone normally has the form of a tunnel with a constant cross-sectional profile over its length from the entrance aperture to the exit aperture. This cross-sectional profile of the detection zone is typically of rectangular, quadratic, circular, or elliptical shape, but can also have any other shape that may be required in a practical application.

Typically in a metal detector according to the invention, the first and second receiver coils and the transmitter coil are wound on a common coil former in the shape of a hollow tube which is made of an electrically insulating non-metallic material and whose inside conforms to the cross-sectional profile of the detection zone.

The space between the coil former and the enclosure may contain sensitive electronic circuit components and is typically filled with a potting compound. The latter has the functions of keeping out moisture and of fixating the coil system and electronic components in their positions relative to the housing.

Metal detectors according to the invention are typically used in packaging- or production lines. Consequently, the scope of the invention also encompasses any packaging- or production line in which the metal detector as claimed, described and/or, illustrated herein is incorporated.

Particularly advantageous is the installation of a metal detector with a one-sided cancelling means as described hereinabove in a processing line where a packaging- or production apparatus unit containing metallic components is arranged immediately upstream of the entrance aperture or downstream of the exit aperture and where no metallic components are present within a metal-free zone extending outside the other aperture. In such a case, the one-sided cancelling means is arranged at the aperture nearest to the apparatus unit containing the metallic components.

In a typical packaging- or production line incorporating a metal detector of the present invention, the latter is arranged so that the tunnel-like detection zone and the travel path of the objects under inspection are oriented in a horizontal direction. The travel path can be constituted by a state-of-the-art conveyor belt.

In another typical packaging- or production line incorporating a metal detector of the present invention, the latter is arranged so that the tunnel-like detection zone and the travel path of the objects under inspection are oriented in a vertical direction. The travel path can be constituted by a chute through which the objects under inspection move in free fall.

BRIEF DESCRIPTION OF THE DRAWINGS

The metal detector according to the invention will hereinafter be explained in more detail through examples and with references to the schematically simplified drawings, wherein.

DETAILED DESCRIPTION

Figure 1:
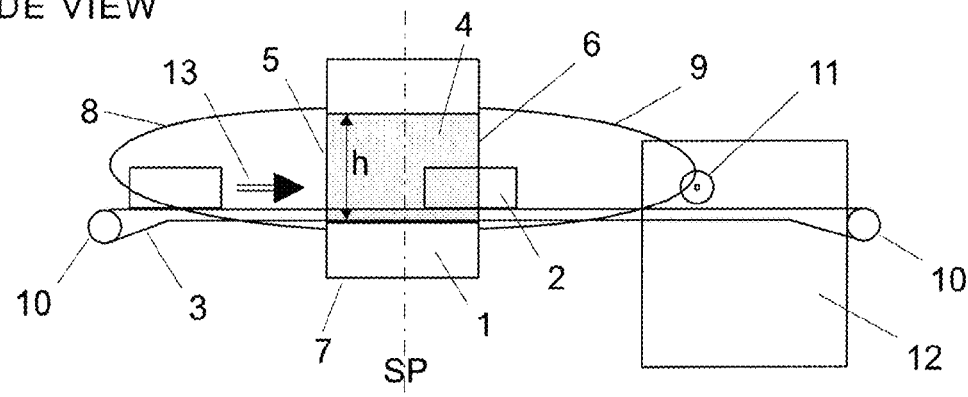
FIG. 1A is a side view of a processing line incorporating a metal detector according to the prior art and a reject punch arranged downstream of the metal detector.
FIG. 1B is a top view of the same processing line.
Figure 1:
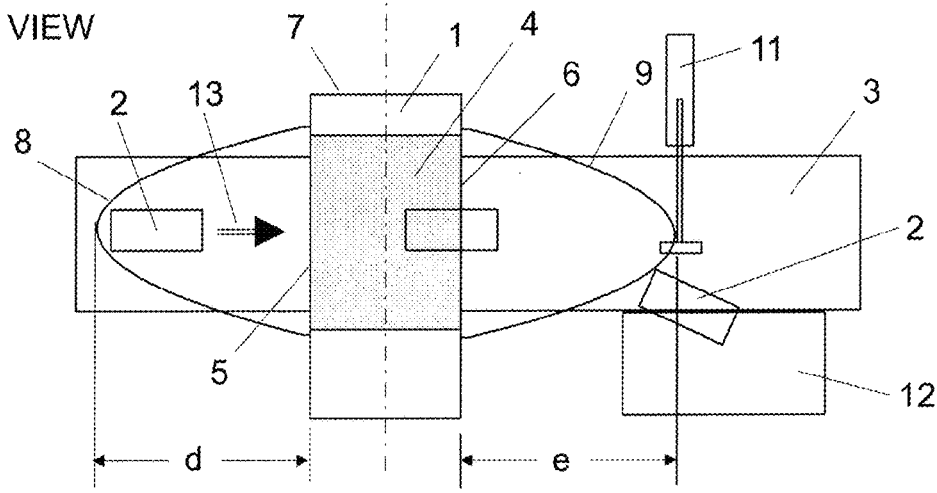

FIG. 1 shows a side view (A.) and a top view (B.) of a processing line incorporating a conventional metal detector 1 according to the state of the art before EP 0 536 288 B1, which serves to detect metal contaminations in articles 2 moving in a direction of travel 13 on a conveyor belt 3 through the detection zone 4 which extends from the entrance aperture 5 to the exit aperture 6 of the metallic enclosure 7. The configuration of the metal detector 1 is symmetric relative to a symmetry plane SP. Substantially equal metal-free zones 8 and 9 extend upstream from the entrance aperture 5 and downstream from the exit aperture 6. Metallic parts of the processing line are placed outside the periphery of the metal-free zones 8 and 9. In the illustrated example this concerns specifically apparatus units such as the belt rollers 10 and the reject punch mechanism 11 which serves to push rejected (i.e. metal-containing) articles off the conveyor belt 3, where they fall into a reject bin 12.

The substantially equal lengths d and e of the metal-free zones 8 and 9 in FIGS. 1A and 1B are realistically proportioned in relation to the aperture height h and to the length z of the metal detector enclosure. This illustrates the substantial space allowance that has to be made for the metal-free zones 8 and 9, unless one opts for a ZMFZ-solution according to EP 0 536 288 B1, where the metal-free zones on both sides of the metal detector are equally suppressed. However, as explained previously herein, this comes at the expense of a somewhat lower detection sensitivity for metal contaminants inside the detection zone 4.

Figure 2:
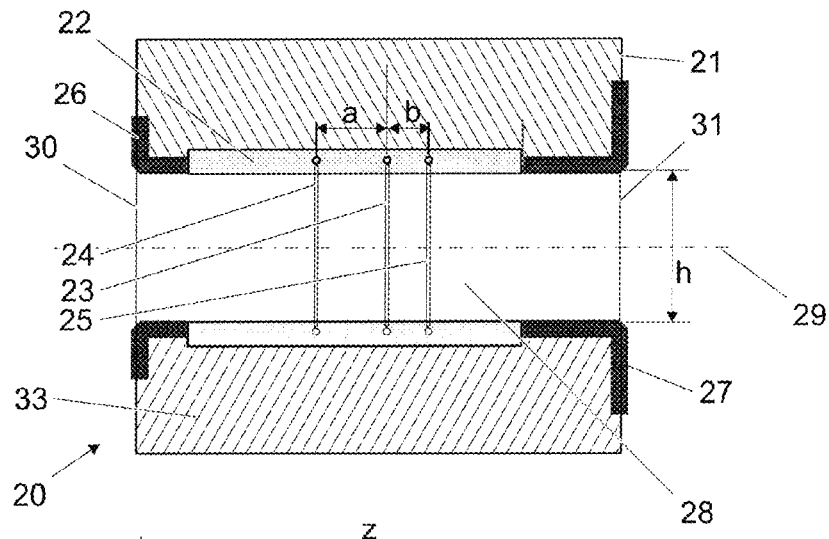
FIG. 2 schematically illustrates a preferred embodiment of the metal detector according to the present invention in a sectional view.

FIG. 2 represents a first embodiment of a metal detector 20 according to the present invention in a vertical sectional plane along a central axis 29. For clarity and consistency, the metal detector 20 is shown with the same orientation as the metal detector 1 of FIG. 1, i.e. with its entrance aperture 30 facing to the left side and its exit aperture 31 facing to the right side of FIG. 2. The principal parts of the metal detector 20 are the enclosure 21, the coil former 22 with the transmitter coil 23 and receiver coils 24, 25, and aperture flanges 26, 27 at the entrance and exit apertures 30, 31, respectively. The coils 23, 24, 25 are imbedded in the coil former 22, and the rotary direction of the coil windings is reversed between the first receiver coil 24 and the second receiver coil 25. With the exit aperture flange 27 being substantially larger than the entrance aperture flange 26, the metal detector 20 in the embodiment of FIG. 2 exemplifies an asymmetric ZMFZ concept as explained previously herein. The enclosure 21 and the aperture flanges 26, 27 must be made of metal in order to perform their function of confining the primary magnetic field generated by the transmitter coil 23. The coil former 22, on the other hand, must be made of a non-conductive but mechanically stable material such as, e.g., a fiber-reinforced plastic. The coil former 22, the aperture flanges 26, 27, and the entrance and exit apertures 30, 31 form a tunnel-like detection zone 28 through which a product under inspection (not shown in the drawing) moves for example on a conveyor belt, entering the metal detector 20 through the entrance aperture 30 and leaving the metal detector 20 through the exit aperture 31. The inside space contained between the enclosure 21, the coil former 22 and the aperture flanges 26, 27 is filled with a potting compound 33 which serves to keep out moisture and to hold the coil former 22, the aperture flanges 26, 27 and the enclosure 21 rigidly in place relative to each other. For installations with a conveyor belt, where the central axis 29 of the metal detector 20 is oriented horizontally, the cross-sectional profile of the detection zone 28 is preferably rectangular, and the dimension h indicates in this case the aperture height. However, other orientations and other profile shapes of the detection zone are likewise possible, for example a round, vertically oriented detection zone through which the products under inspection move in free fall through a chute-like detection zone 28. In this case, the dimension h would indicate the aperture diameter.

The aperture flanges 26, 27 act as short-circuit coils in which a current is induced by the alternating or pulsating primary electromagnetic field of the transmitter coil 23. According to Lenz's rule, an induced current always flows in such a direction as to oppose the field change that causes it. Accordingly, the secondary electromagnetic field generated by the induced current in the aperture flanges 26, 27 opposes the primary field. This applies especially to those parts of the aperture flanges 26, 27 that are aligned horizontally in FIG. 2. Depending on the design and dimensions of the aperture flanges 26, 27, the secondary electromagnetic field can reduce or even totally cancel the primary field of the transmitter coil to the outside of the entrance and exit apertures 30, 31.

The transmitter coil 23 is preferably positioned in the center of the length z of the detection zone 28. The first and second receiver coils 24, 25 are placed asymmetrically, i.e. at different respective distances a and b from the transmitter coil 23. The distances a and b are determined, e.g., experimentally or by computer modeling, with the simultaneous objectives of optimizing the detection sensitivity and balancing the induced voltages in the receiver coils against each other.

Alternatively the transmitter coil 23 can be positioned out of center between the entrance aperture 30 and the exit aperture 31 whereas the first receiver coil 24 and the second receiver coil 25 are arranged each at a different distance a, b from the transmitter coil 23 but not necessarily from said center of the length z of the detection zone 28.

However, in some applications, one or both of the aperture flanges 26, 27 can extend outside the metal enclosure 21 (not shown in the figures) and form a collar which is connected to or integral with the rim of one of the enclosure apertures 30, 31.

Figure 3A:
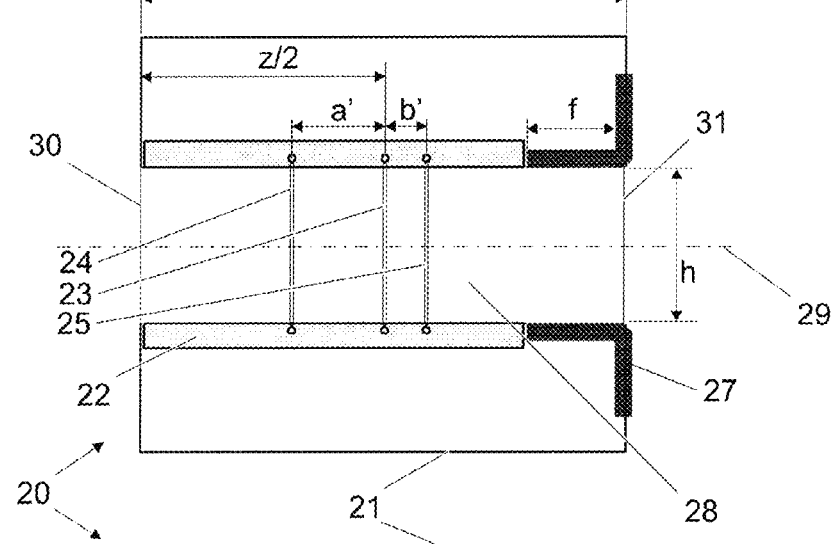
FIG. 3A illustrates a special case of the metal detector of FIG. 2 with only one aperture flange.
Figure 3B:
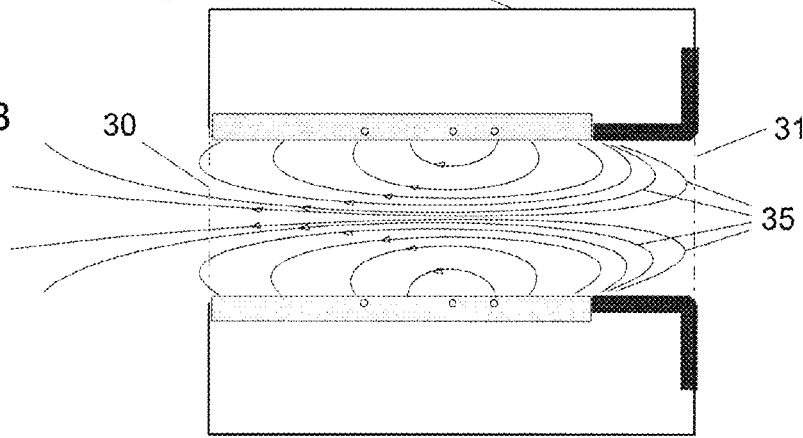
FIG. 3B shows the metal detector of FIG. 3A with field lines of the primary electromagnetic field.

FIGS. 3A and 3B illustrate a special case of the metal detector of FIG. 2, where one of the aperture flanges, in this case the flange 26 at the entrance aperture 30, has been completely left out. Rather than solving the problems of optimizing the detection sensitivity and balancing the induced voltages in the receiver coils simultaneously, one could in this case start by placing the first receiver coil 24 at a distance a' which is selected so as to maximize the detection sensitivity. Next, the second receiver coil 25, i.e. the coil on the side with the aperture flange 27, is positioned relative to the transmitter coil 23 at a distance b' where the respective voltages induced in the receiver coils 24, 25 by the primary field cancel each other when there is no metal being detected in the detection zone. The distance b' will generally be smaller than a' and will depend on the flange length f and aperture height h.

The effect of the secondary field of the aperture flange 27 on the primary electromagnetic field of the transmitter coil 23 is illustrated in FIG. 3B for the same metal detector 20 as shown in FIG. 3A. To the outside of the exit aperture 31, the primary field generated by the transmitter coil 23 is essentially cancelled by the secondary field of the aperture flange 27. This is graphically illustrated by the field lines 35. For the sake of clarity, field lines reaching into the potted section 33 of the enclosure 21 are not shown.

Field lines on the side of the exit aperture 31 are deflected back into the detection zone 28. In contrast, the primary field is not opposed by a secondary field on the opposite side of the detection zone 28. Therefore, the same field lines 35 that are deflected back on the exit side extend undeflected through the entrance aperture 30 to the outside of the metal detector 20. As a result, the metal detector 20 requires essentially no metal-free zone at the exit aperture 31, while a standard metal-free zone extending about as far as 1.5 to 2.5 times the aperture height h is required outside the entrance aperture 30.

Figure 4:
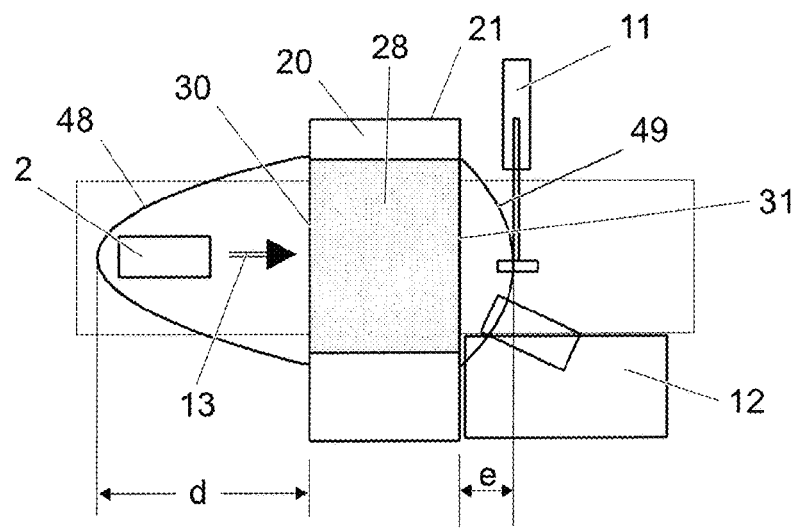
FIG. 4 shows a top view of a processing line incorporating a metal detector according to the invention and a reject punch arranged downstream of the metal detector.

FIG. 4 shows a top view of a processing line incorporating the asymmetric metal detector 20 of FIGS. 3A and 3B. To allow an easy comparison, FIG. 4 is placed on the same page and drawn to the same scale as FIG. 1. While the metal-free zone 48 on the entrance side of the metal detector 20 extends to the same first distance d as the symmetric metal-free zones 8 and 9 of the metal detector 1 in FIG. 1, the metal-free zone 49 on the exit side is now substantially shorter, extending to a second distance e≈d/4 in the illustrated example. This makes it possible to arrange the reject punch mechanism 11 practically next to the exit aperture 31, so that the metal detector 20 according to the invention can be installed in a significantly shorter insertion space than the conventional metal detector 1. At the same time, as the metal detector 20 employs the ZMFZ concept only on one side, the useful detection sensitivity of the metal detector 20 is not appreciably diminished in comparison to the conventional metal detector 1.

While the invention has been described through the presentation of specific examples, it is evident that, based on the knowledge provided by the present disclosure, the invention could be embodied in numerous other variations with asymmetric field-cancelling means, where the field-cancelling means on the entrance side of the metal detector is different from the field-cancelling means on the exit side in order to achieve reductions of the respective metal-free zones as required for a given installation, while retaining the highest possible degree of useful sensitivity of the metal detector. Furthermore, a means for cancelling the primary field could also be a coil that is actively energized by an electronic circuit, in contrast to the metallic flanges or collars which are passive carriers of induced currents.

Further embodiments of the invention are conceivable using other state of the art symmetrical balance coil arrangements that consist of multiple transmitter and/or multiple receiver coils that are arranged asymmetrically to achieve the null balance condition and optimized sensitivity within the asymmetric ZMFZ configuration.

It should be understood that all such variations and combinations are considered to be within the scope of the present invention.

What is claimed is:

1. A detector for inspecting an object for the presence of metal, comprising:
   a metallic enclosure having an entrance aperture through which an object being inspected enters the enclosure and an exit aperture through which the object exits the enclosure, the respective apertures defining a travel direction;
   a coil system, arranged inside the enclosure, the coil system comprising:
      at least one transmitter coil, arranged to generate a primary electromagnetic field when energized by an alternating electric current;
      at least one first receiver coil, arranged so that the primary electromagnetic field induces a first voltage therein; and
      at least one second receiver coil, arranged so that the primary electromagnetic field induces a second voltage therein, the respective receiver coils bounding a detection zone, extending between the entrance and exit apertures, through which the object being inspected moves;
      wherein the first and second receiver coils are arranged asymmetrically relative to the transmitter coil, with the first receiver coil positioned, relative to the travel direction, at a first predetermined distance ahead of the transmitter coil and the second receiver coil positioned at a second predetermined distance after the transmitter coil, the first and second predetermined distances being different;
      wherein the respective receiver coils are connected in series, the wires of the respective receiver coils wound with the opposite sense of rotation relative to each other; and
   at least one of: a first cancelling means and a second cancelling means for cancelling an electromagnetic field, the first cancelling means arranged at the entrance aperture to cancel the primary electromagnetic field beyond a predetermined first distance from the coil system, and the second cancelling means arranged at the exit aperture to cancel the primary electromagnetic field beyond a predetermined second distance from the coil system, such that, when both the first cancelling means and the second cancelling means are present, the respective cancelling means are different from each other and the respective first and second distances are likewise different from each other, and
   that the first and second induced voltages are in a balanced state with each other when no metal is present in the objects under inspection.

2. The detector of claim 1, wherein:
   the transmitter coil is positioned in a central plane between the entrance aperture and the exit aperture.

3. The detector of claim 1, wherein:
   only one of the respective cancelling means is present, at the associated aperture, such that the primary electromagnetic field is cancelled in only one direction beyond the associated predetermined distance from the coil system, the primary electromagnetic field being essentially undiminished in the other direction.

4. The detector of claim 3, wherein:
   the transmitter coil is placed at an intermediate position between the respective apertures;
   the receiver coil that is next to the aperture that has no cancelling means is placed at a position that optimizes the sensitivity of the coil system to metal contaminants in the object under inspection; and
   the receiver coil that is next to the aperture with the cancelling means is placed at a position such at the first and second induced voltages cancel each other when there is no metal present in the object under inspection.

5. A line for packaging or production, comprising:
   an apparatus unit that contains metallic components; and
   a detector for inspecting an object for the presence of metal, according to claim 3, arranged in the line with the apparatus unit with either the entrance or exit aperture of the detector arranged so adjacent to the apparatus unit, such that no metallic components are present within a metal-free zone that extends outside of the other aperture, with the one cancelling means arranged at the aperture adjacent to the apparatus unit.

6. The line for packaging or production of claim 5, wherein:
   the detector is oriented such that a travel path of the object under inspection passes horizontally through the detector.

7. The line for packaging or production of claim 6, wherein:
   the travel path comprises a conveyor belt.

8. The detector of claim 1, wherein:
   the predetermined first distance delimits a first metal-free zone upstream of the metal enclosure in the travel direction; and the predetermined second distance delimits a second metal-free zone downstream of the metal enclosure in the travel direction.

9. The detector of claim 1, wherein:
each of the respective cancelling means comprises a metallic flange or collar, connected to or integral with a rim of the aperture with which it is associated, the flange or collar acting as a short-circuit coil such that a current induced in the flange or collar by the primary electromagnetic field generates a secondary electromagnetic field that nullifies the primary electromagnetic field beyond the associated predetermined distance.

10. The detector of claim 1, wherein:
the detection zone is in the form of a tunnel having a constant cross-sectional profile along a length from the entrance aperture to the exit aperture.

11. The detector of claim 10, wherein:
the cross-sectional profile is rectangular.

12. The detector of claim 10, wherein:
each of the receiver coils and the transmitter coil is wound on a common coil former in the shape of a hollow tube, the common coil former being made of an electrically insulating non-metallic material with an inside shape that conforms to the cross-sectional profile of the detection zone.

13. A line for packaging or production, comprising:
the detector according to claim 1.

14. The line for packaging or production of claim 13, wherein:
the detector is oriented such that a travel path of the object under inspection passes horizontally through the detector.

15. The line for packaging or production of claim 14, wherein:
the travel path comprises a conveyor belt.

* * * * *